United States Patent [19]

Tanaka

[11] Patent Number: 5,149,504
[45] Date of Patent: Sep. 22, 1992

[54] APPARATUS FOR ASSESSING GAS ODOR INTENSITY

[76] Inventor: Toshiaki Tanaka, 478, Banba-cho, Shimokanuki, Numazu-shi, Shizuoka-ken, Japan

[21] Appl. No.: 773,439

[22] Filed: Oct. 9, 1991

Related U.S. Application Data

[63] Continuation of Ser. No. 419,589, Oct. 10, 1989.

[30] Foreign Application Priority Data

Oct. 20, 1988 [JP] Japan .................. 63-265107

[51] Int. Cl.$^5$ ................ G01N 33/22; G01N 27/00
[52] U.S. Cl. ........................... 422/88; 422/83; 73/23.31; 73/23.34
[58] Field of Search .............. 73/23.31, 23.34; 436/137; 422/83, 88

[56] References Cited

U.S. PATENT DOCUMENTS 3,114,610 12/1963 Gafford ................. 463/163

OTHER PUBLICATIONS

P. L. Levins et al., "Chemical Analysis of Diesel Exhaust Odor Species", SAE Paper 740216, 1974, pp. 1-11.

Kato et al., "A method for measuring the odor intensity of exhaust gas from a diesel engine", Transactions of the society of Automotive Engineers of Japan, Oct. 1977, pp. 1-23.

Primary Examiner—David L. Lacey
Assistant Examiner—David Redding

[57] ABSTRACT

A method and apparatus for assessing the odor intensity of combustion gas produced from an internal combustion engine in which the odor intensity of combustion gas is obtained from the pH-value of an aqueous solution prepared from odor-producing substances, based on a predetermined relationship between pH-value and odor intensity. The odor intensity thus obtained strongly correlates with organoleptically evaluated odor intensity. Since the odor intensity of the gas is determined from the pH-value, the precision and the reliability of the odor intensity measurement are enhanced.

6 Claims, 8 Drawing Sheets

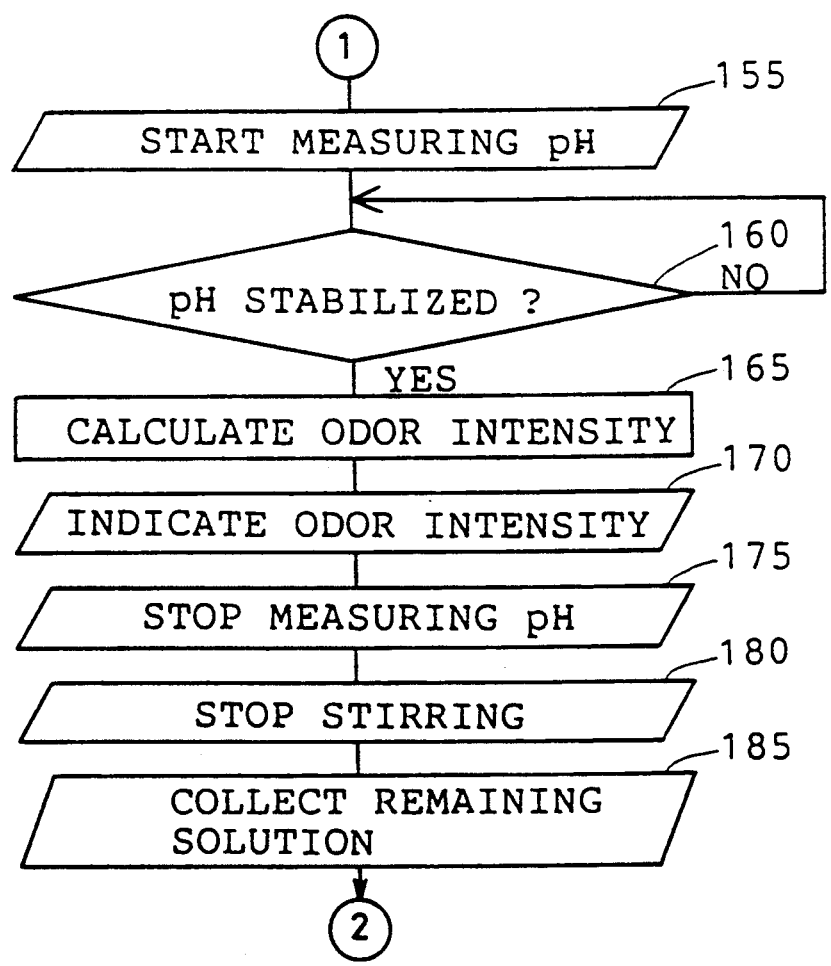

APPARATUS FOR ASSESSING GAS ODOR INTENSITY

This is a continuation of application Ser. No. 07/419,589 filed Oct. 10, 1989, pending.

BACKGROUND OF THE INVENTION

This invention relates to a method of assessing the odor intensity of gas which can be effectively used in lieu of an organoleptic odor intensity evaluation.

It is known that an organoleptic evaluation is appropriate for measuring the odor intensity of gas. However, an organoleptic evaluation of the odor intensity of gas cannot be consistently performed in an industrial setting. Accordingly, other methods for evaluating the odor intensity of gas have been developed.

For example, a method for measuring the odor intensity of exhaust gas from a diesel engine was proposed in a lecture reported in the Transactions of the Society of Automotive Engineers of Japan, which was authored by Kato et al. and published in October, 1977. In this method, formaldehyde is quantitatively analyzed as an odor-producing substance. In their results, the actual concentration of formaldehyde best correlates with the organoleptically evaluated odor intensity. It was reported that the correlation between all the organoleptically evaluated odor intensities of exhaust gas from four types of diesel engines and the concentrations of formaldehyde in the exhaust gas is 0.54. Therefore, Kato et al. proposed quantitatively measuring odor intensity of diesel exhaust by measuring the concentration of formaldehyde in the exhaust gas.

This strong correlation between the concentration of formaldehyde and the organoleptically evaluated odor intensity can be obtained when the data of all the diesel engines tested is analyzed. However, when the odor intensity of the exhaust gas from a specific engine is measured, the concentration of formaldehyde does not always correlate with the organoleptically evaluated odor intensity. Since various compounds in the exhaust gas produce odor, the odor intensity of the gas cannot be precisely measured by measuring the concentration of formaldehyde alone.

For example, the concentration of formaldehyde in the exhaust gas from a diesel engine running for a long time, a direct-injection diesel engine running for a short time, or a diesel engine with an auxiliary combustion chamber running for a short time may not correlate with the organoleptically evaluated odor intensity of the exhaust gas.

By this prior-art method, the odor intensity of the exhaust gas from a diesel engine or that of the air exhausted from an air conditioner cannot be quantitatively measured, since the formaldehyde does not correlate with the organoleptically evaluated odor intensity.

SUMMARY OF THE INVENTION

The object of this invention is to provide a method and apparatus for assessing the odor intensity of gas so that the measured intensity strongly correlates with the organoleptically evaluated intensity.

To achieve this object, the present invention provides a method and apparatus for assessing measuring the odor intensity of gas. As shown in FIG. 1, the method comprises the steps of capturing odor-producing substances from specimen gas and preparing an aqueous solution from the substances (S1); measuring the hydrogen-ion concentration of the aqueous solution (S2); and calculating the odor intensity from the hydrogen-ion concentration based on the predetermined relationship between the hydrogen-ion concentration and the odor intensity of the gas (S3).

BRIEF DESCRIPTION OF THE DRAWINGS

FIGS. 3A and 3B compose a flowchart indicating the odor-intensity measuring processes executed in the first embodiment.

DETAILED DESCRIPTION OF PREFERRED EMBODIMENTS

Figure 1:
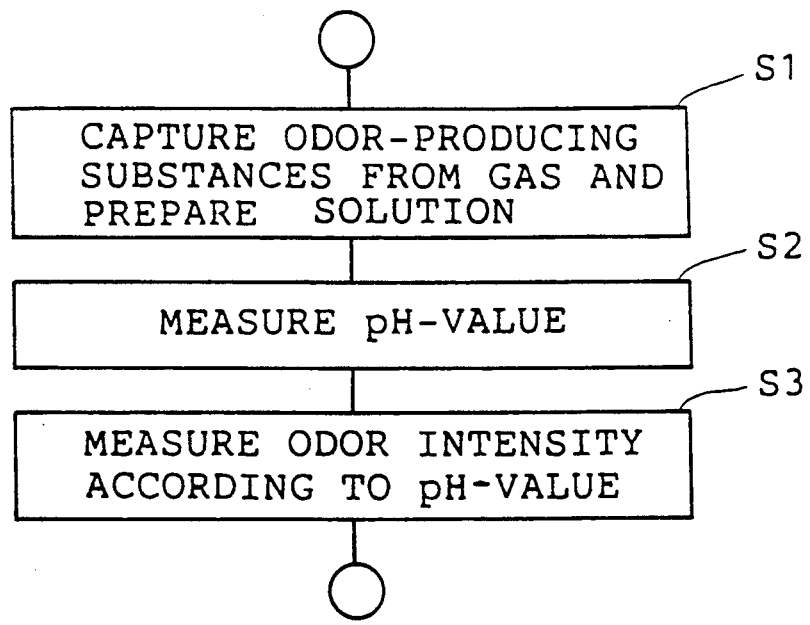
FIG. 1 is a flowchart indicating the fundamental processes of the present invention.
Figure 2:
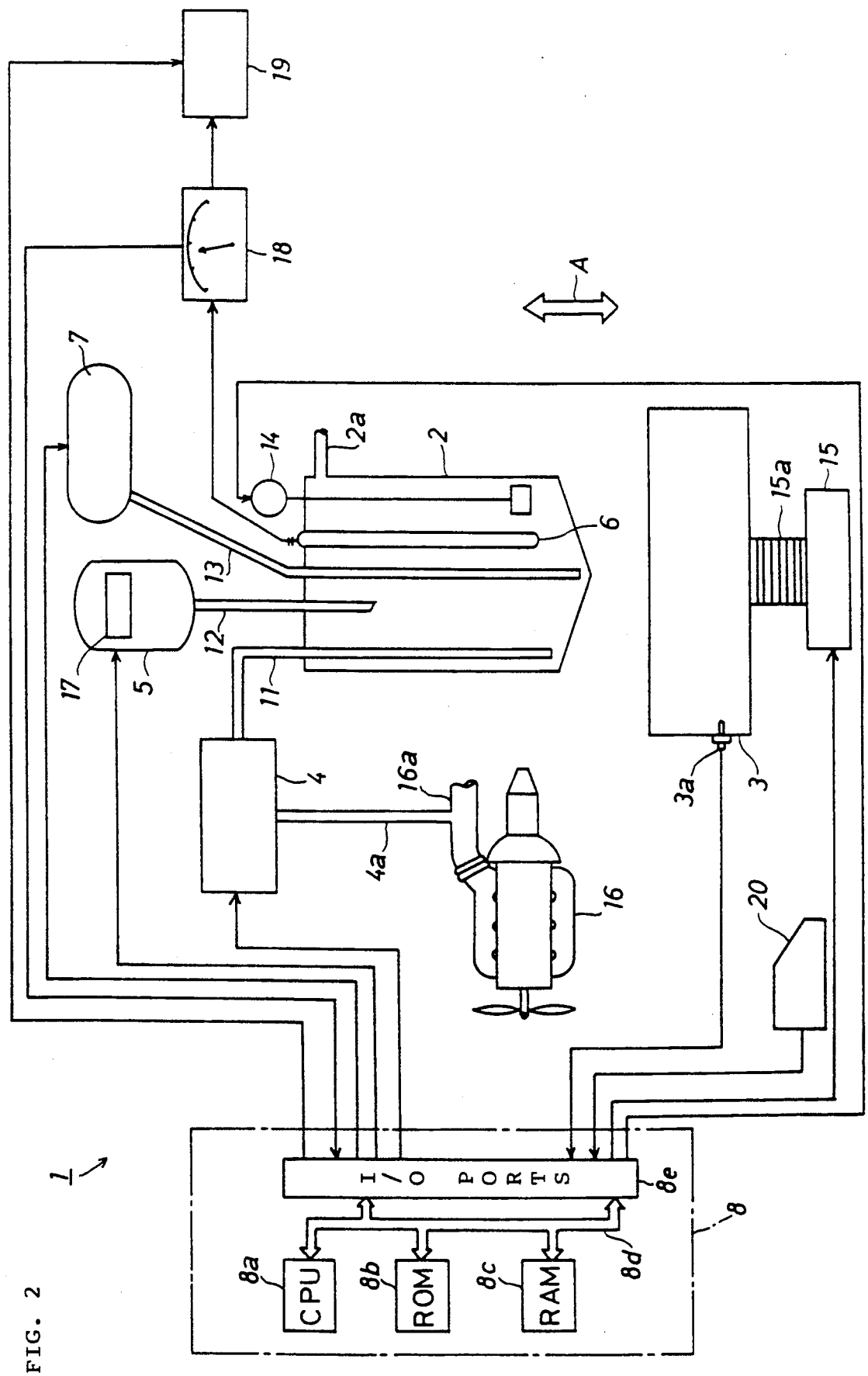
FIG. 2 is a block diagram showing the structure of the first embodiment.

In a first embodiment shown in FIG. 2, an exhaust-gas analyzer 1 comprises a reactor 2 for preparing an aqueous solution from exhaust gas to be measured for odor intensity, a refrigerator 3 for cooling the reactor 2, an exhaust-gas tank 4 for introducing exhaust gas as a specimen into the reactor 2, and a water supplier 5 for supplying demineralized water to the reactor 2. The exhaust-gas analyzer 1 further comprises a pH-value measuring apparatus 6 for measuring the hydrogen-ion concentration (referred to as pH-value hereinafter) of the aqueous solution in the reactor 2, a drainage tank 7 for collecting the remaining solution through drainage pipe 13 from the reactor 2 after the measurement of the pH-value, and an electronic controller 8 for controlling the exhaust-gas tank 4, the water supplier 5, and the drainage tank 7.

The reactor 2 is an almost cylindrical container having a port 2a that opens to the outside. The exhaust-gas tank 4 supplies specimen exhaust gas through an exhaust-gas pipe 11 to the reactor 2, in response to a direction from the electronic controller 8. The electronic controller 8 directs the water supplier 5 to supply demineralized water through a water pipe 12 to the reactor 2. The reactor 2 has a stirrer 14, which mixes the aqueous solution in the reactor 2 according to a direction from the electronic controller 8, to homogenize the concentration of the solution.

An elevator 15 comprises a motor for driving the elevator 15 in response to the electronic controller 8 and a power-transmitting mechanism 15a. The elevator 15 lifts and lowers the refrigerator 3 vertically as indicated by an arrow A in FIG. 2. The refrigerator 3 contains a refrigerant such as dry ice, alcohol, or diethylene glycol, which is stored at about $-50°$ C. The refrigerator 3 comprises a temperature sensor 3a with a thermistor for detecting the temperature of the refrigerant.

Under the control of the electronic controller 8, the exhaust-gas tank 4 receives a predetermined amount of exhaust gas through a bypass 4a providing an auxiliary passage from an exhaust pipe 16a of a direct-injection diesel engine 16, and supplies the gas through the exhaust-gas pipe 11 to the reactor 2.

The water supplier 5 has a pH-value controller 17 for maintaining the pH-value of demineralized water within the range of pH5.6±0.2, and supplies the demineralized water to the reactor 2 in response to a direction from the electronic controller 8.

The pH-value measuring apparatus 6 has a glass, quinhydrone, or antimony electrode. The pH-value measuring apparatus 6 measures pH-value by measuring electric potential differences, and transmits the pH-value to an indicator 18 and the electronic controller 8.

After the pH-value is measured, under the control of the electronic controller 8, the drainage tank 7 collects the remaining solution by means of a pump (not shown) from the reactor 2 through drainage pipe 13.

The electronic controller 8 is a microcomputer consisting of a known CPU 8a, known ROM 8b, and known RAM 8c, which are connected via a common bus 8d to I/O ports 8e. The detection signals from the pH-value measuring apparatus 6 and the temperature sensor 3a are transmitted through the input/output ports 8e to the CPU 8a. The CPU 8a transmits control signals through the input/output ports 8e to the exhaust-gas tank 4, the water supplier 5, the drainage tank 7, the stirrer 14, and the elevator 15. The electronic controller 8 operates in response to directions from an input unit 20 and transmits the odor intensity of the exhaust gas to an odor-intensity indicator 19.

Figure 3A:
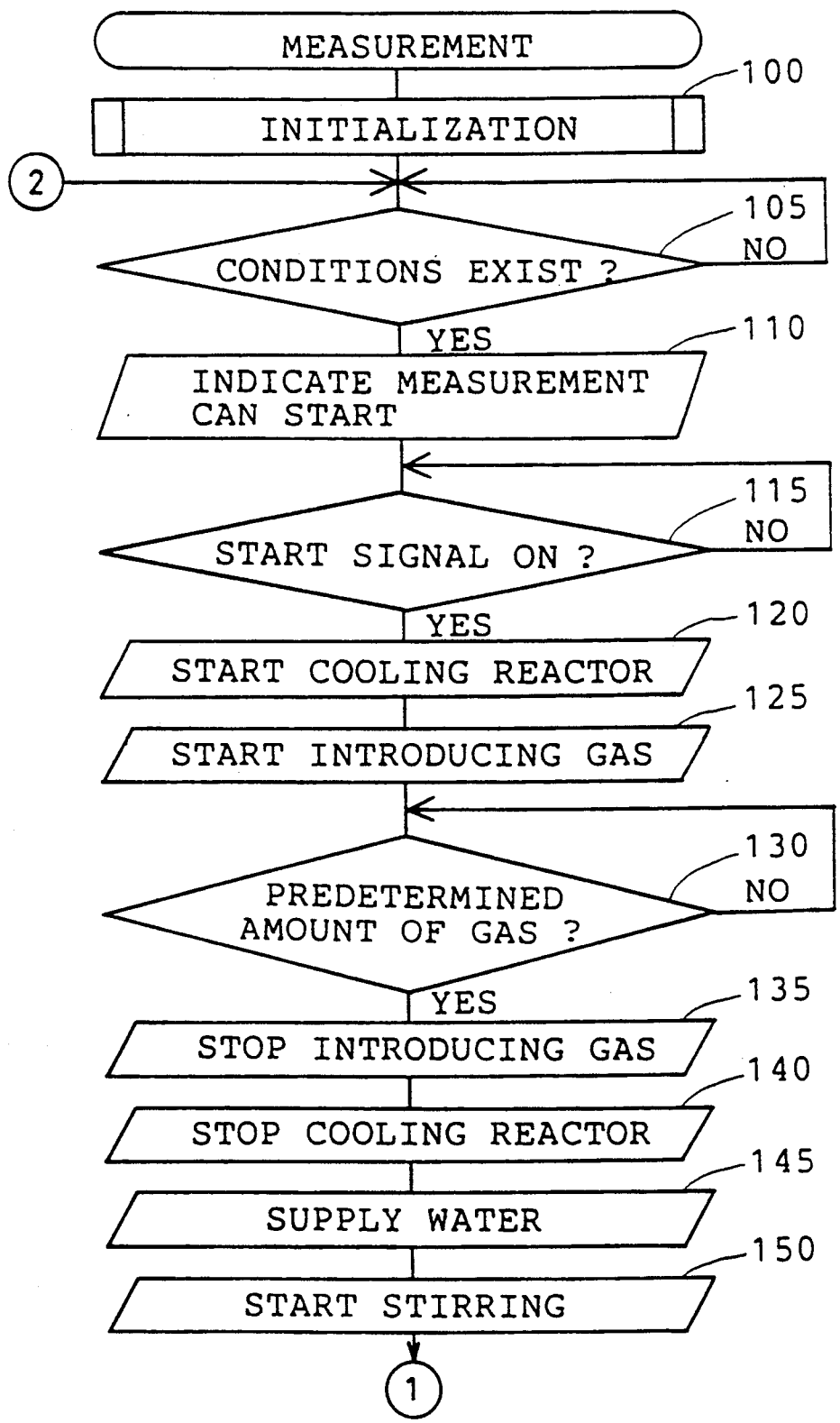

The method for measuring the odor intensity of the exhaust gas is outlined in the flowchart in FIGS. 3A and 3B. When the electronic controller 8 is turned on, the measurement starts.

First, step 100 reads and sets the conditions fed from the input unit 20, such as the temperature of the refrigerant in the refrigerator 3, the amount of the exhaust gas to be supplied to the reactor 2, and the amount of demineralized water to be supplied to the reactor 2. Subsequently, step 105 determines whether or not the conditions for starting the measurement exist. These conditions include desired refrigerant temperature, rate of introducing exhaust gas, rate of supplying demineralized water, and duration of the test period.

When the conditions exist, the process goes to step 110. On the other hand, when the conditions do not exist, step 105 is repeated until the conditions are established.

At step 110, the electronic controller 8 indicates on the input unit 20 that the exhaust-gas analyzer 1 can start the measurement, and instructs the operator to press a start switch. Subsequently, step 115 determines whether the start switch on the input unit 20 has been pressed and the operation start signal has been issued. Step 115 is repeated until the operation start signal has been issued. If the operation start signal has been issued, the process goes to step 120. Step 120 transmits a control signal to the elevator 15 to lift the refrigerator 3 and start cooling the reactor 2. Subsequently, step 125 transmits a control signal to the exhaust-gas tank 4 to start introducing the specimen exhaust gas into the reactor 2.

Step 130 determines whether or not the reactor 2 has received the amount of exhaust gas predetermined at step 100. Since the exhaust-gas tank 4 introduces exhaust gas at a constant rate, step 130 determines whether the predetermined amount of exhaust gas has been supplied to the reactor 2 based on how much time has elapsed since the exhaust-gas tank 4 started introducing the exhaust gas. Step 130 is repeated until the predetermined amount of exhaust gas has been introduced into the reactor 2. When the predetermined amount of exhaust gas has been introduced to the reactor 2, the process goes to step 135.

Step 135 sends a control signal to the exhaust-gas tank 4 to stop introducing exhaust gas, and step 140 sends a control signal to the elevator 15 to lower the refrigerator 3 to stop cooling the reactor 2.

Through steps 100–140, odor-producing substances in the exhaust gas condense because of the refrigeration, but carbon dioxide ($CO_2$) in the exhaust gas does not condense. The odor-producing substances are thus separated from the rest of the exhaust gas.

Subsequently, step 145 sends a control signal to the water supplier 5 to supply demineralized water to the reactor 2. An aqueous solution is thus prepared from the odor-producing substances. Step 150 sends a control signal to the stirrer 14 to stir the solution in the reactor 2 so that the concentration of odor-producing substances in the solution is made uniform. Step 155 sends a control signal to the pH-value measuring apparatus 6 to start measuring the pH-value. Next, step 160 determines whether or not the pH-value detected by the pH-value measuring apparatus 6 has stabilized. If the pH-value has become stable, the process goes to step 165. If not, step 160 is repeated until the pH-value becomes stable. Step 165 calculates the odor intensity based on the measured pH-value using the values stored in the ROM 8b.

Figure 4:
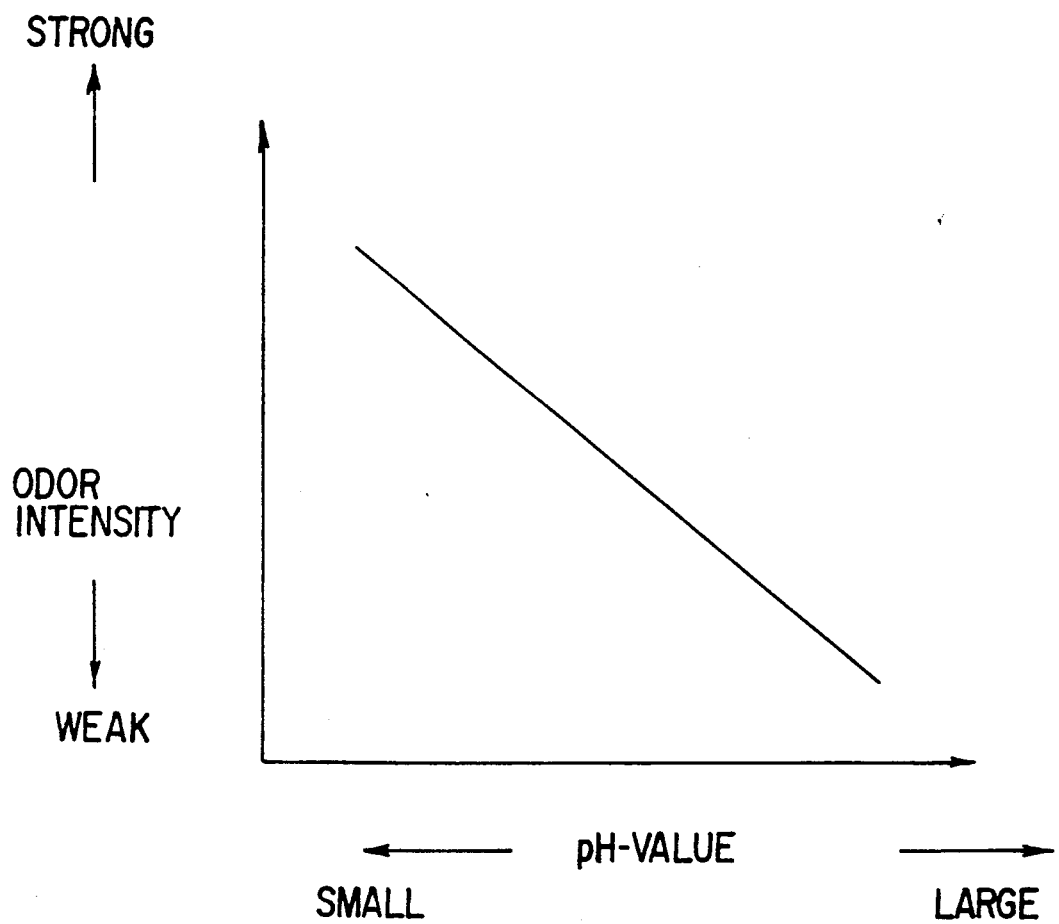
FIG. 4 is a graph indicating the relationship between organoleptically evaluated odor intensity and pH-value.

The values stored in ROM 8b are generally represented by the graph in FIG. 4. The graph in FIG. 4 is calculated by plotting the organoleptically evaluated odor intensity of specimens of gas with varying odor intensities against the pH-value of an aqueous solution prepared from the odor-producing substances of each gas specimen. Thus, the graph represents the predetermined relationship between hydrogen-ion concentration and the odor intensity of the gas.

Step 170 sends a control signal to the odor-intensity indicator 19 to indicate the odor intensity calculated at step 165. Step 175 sends a control signal to the pH-value measuring apparatus 6 to stop measuring the pH-value, then step 180 sends a control signal to the stirrer 14 to stop stirring the aqueous solution in the reactor 2. After step 185 sends a control signal to the drainage tank 7 to collect the remaining aqueous solution from the reactor 2, the process returns to step 105. When the start switch on the input unit 20 is pressed again, the measuring processes of steps 100–185 are repeated.

In this first embodiment, the measurement of the odor intensity of the exhaust gas from the direct-injection diesel engine 16 correlates with the organoleptic evaluation of the odor intensity.

The odor intensity of the exhaust gas from the direct-injection diesel engine 16 is quantitatively calculated using the predetermined graph showing the relationship between pH-value and odor intensity. This quantitative analysis of odor intensity enhances the precision and the reliability of the organoleptic evaluation of odor intensity.

In the first embodiment, when the aqueous solution to be measured is prepared from exhaust gas introduced into the reactor 2, the reactor 2 is cooled to a temperature of about −40° C. to −50° C. so that $CO_2$ does not condense; only the odor-producing substances condense. The influence of $CO_2$ on the measurement can thus be avoided, and the odor intensity can be more precisely obtained.

By repeating the processes of cooling the reactor 2, introducing the exhaust gas, preparing the aqueous solution, measuring the pH-value, and collecting the residual solution from the reactor 2, the odor intensity can be consistently and accurately measured.

The aqueous solution can also be prepared by spraying the exhaust gas on a polar adsorbent such as alumina, and then spraying demineralized water on the polar absorbent. By this method, the same effect as that obtained in the first embodiment results.

The aqueous solution can also be prepared by introducing exhaust gas directly into demineralized water in the form of bubbles. By this method, when the graph of the relationship between the pH-value and the odor intensity perceived is adjusted according to the amount of $CO_2$ mixed in the solution, pH-value measurement errors of the pH-value caused by $CO_2$ in the solution can be eliminated.

In the first embodiment, demineralized water with pH5.6±0.2 is used to prepare the aqueous solution. Alternatively, a stabilizer can be added to the aqueous solution.

In the first embodiment, a batch measurement is made using the reactor. However, a second embodiment, shown in FIG. 5, continuously measures the pH-value using a looped belt.

Figure 5:
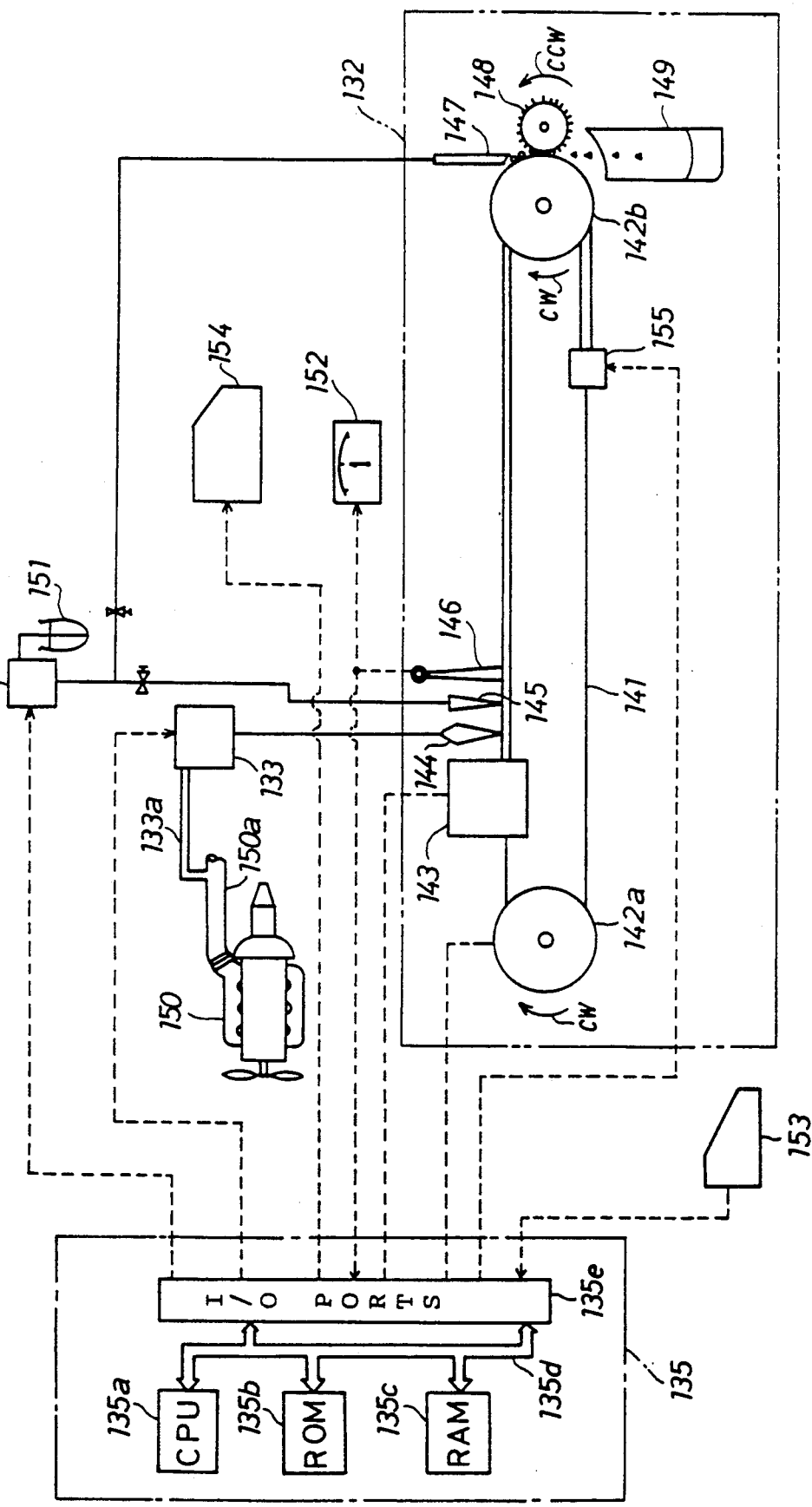
FIG. 5 is a block diagram showing the structure of the second embodiment.

As shown in FIG. 5, an exhaust-gas analyzer 131 for the second embodiment comprises a movable reactor 132, an exhaust-gas tank 133 for introducing exhaust gas into the reactor 132, a water supplier 134 for supplying demineralized water to the reactor 132, and an electronic controller 135 for controlling the reactor 132, the exhaust gas tank 133 and the water supplier 134.

The reactor 132 comprises a bimetallic continuous belt 141, a driving pulley 142a, a driven pulley 142b, a cooling tank 143, an exhaust-gas nozzle 144, a water nozzle 145, a pH-value measuring apparatus 146, a washing nozzle 147, a pulley with bristles 148, a drain container 149 and a heating drier 155. The surface of the bimetallic continuous belt 141 is sensitive to temperature: when it is cooled to about $-80°$ C., its outer surface bends so that it is concave; and when it is heated, it flattens again. The electronic controller 135 controls the driving pulley 142a, which rotates in the direction shown by an arrow CW in FIG. 5, and which drives the belt 141 at a constant speed. The driven pulley 142b also rotates in the direction shown by another arrow CW in FIG. 5, and flattens the belt 141 together with the driving pulley 142a. The cooling tank 143, under the control of the electronic controller 135, cools the belt 141 to about $-80°$ C., thereby bending the outer surface of the belt 141 such that it becomes concave.

The exhaust-gas nozzle 144 sprays the exhaust gas from the exhaust-gas tank 133 over the concave surface of the belt 141. The water nozzle 145 sprays demineralized water from the water supplier 134 on the concave surface of the belt 141 to prepare an aqueous solution on the surface. The pH-value measuring apparatus 146 measures the pH-value of the aqueous solution prepared on the concave surface of the belt 141.

After the pH-value is measured, the washing nozzle 147 washes the surface of the belt 141 using demineralized water. The pulley with bristles 148 rotates in the direction shown by an arrow CCW in FIG. 5 to clean the aqueous solution from the surface of the belt 141, and into the drain container 149. The heating drier 155, under the control of the electronic controller 135, heats the washed belt 141 to about 20° C. to 30° so that the section of the belt 141 flattens again.

Under the control of the electronic controller 135, the exhaust-gas tank 133 receives a predetermined amount of exhaust gas through a bypass 133a, which provides an auxiliary passage from an exhaust pipe 150a of a direct-injection diesel engine 150. The gas is sprayed through the exhaust-gas nozzle 144 to the surface of the belt 141.

The water supplier 134, under the control of the electronic controller 135, receives demineralized water from the reservoir 151, and sprays it through the water nozzle 145 to the surface of the belt 141.

The pH-value measuring apparatus 146 detects the pH-value of the aqueous solution formed on the surface of the belt 141, and sends the pH-value to the electronic controller 135 and to a pH-value indicator 152.

The electronic controller 135 is a microcomputer consisting of a known CPU 135a, a known ROM 135b, and a known RAM 135c, which are connected via a common bus 135d to input/output ports 135e. The detection signals from the pH-value measuring apparatus 146 are transmitted through the CPU 135a transmits control signals through the input/output ports 135e to the exhaust-gas tank 133, the water supplier 134, the driving pulley 142a, the cooling tank 143, and the heating drier 155. The electronic controller 135 operates in response to a direction from an input unit 153, and transmits the odor intensity measurement for the exhaust gas to a printer 154.

Figure 6A:
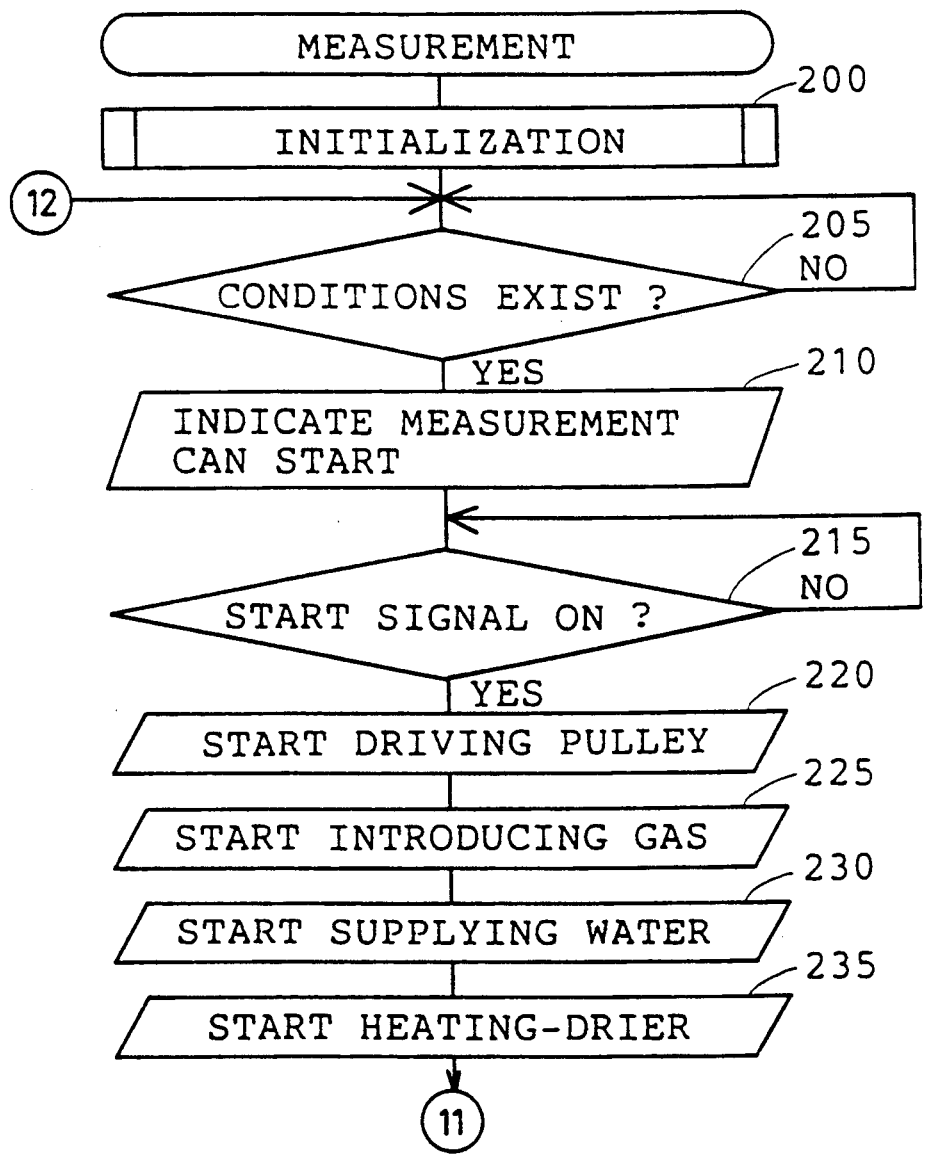
FIGS. 6A and 6B compose a flowchart indicating odor-intensity measuring processes executed in the second embodiment.
Figure 6B:
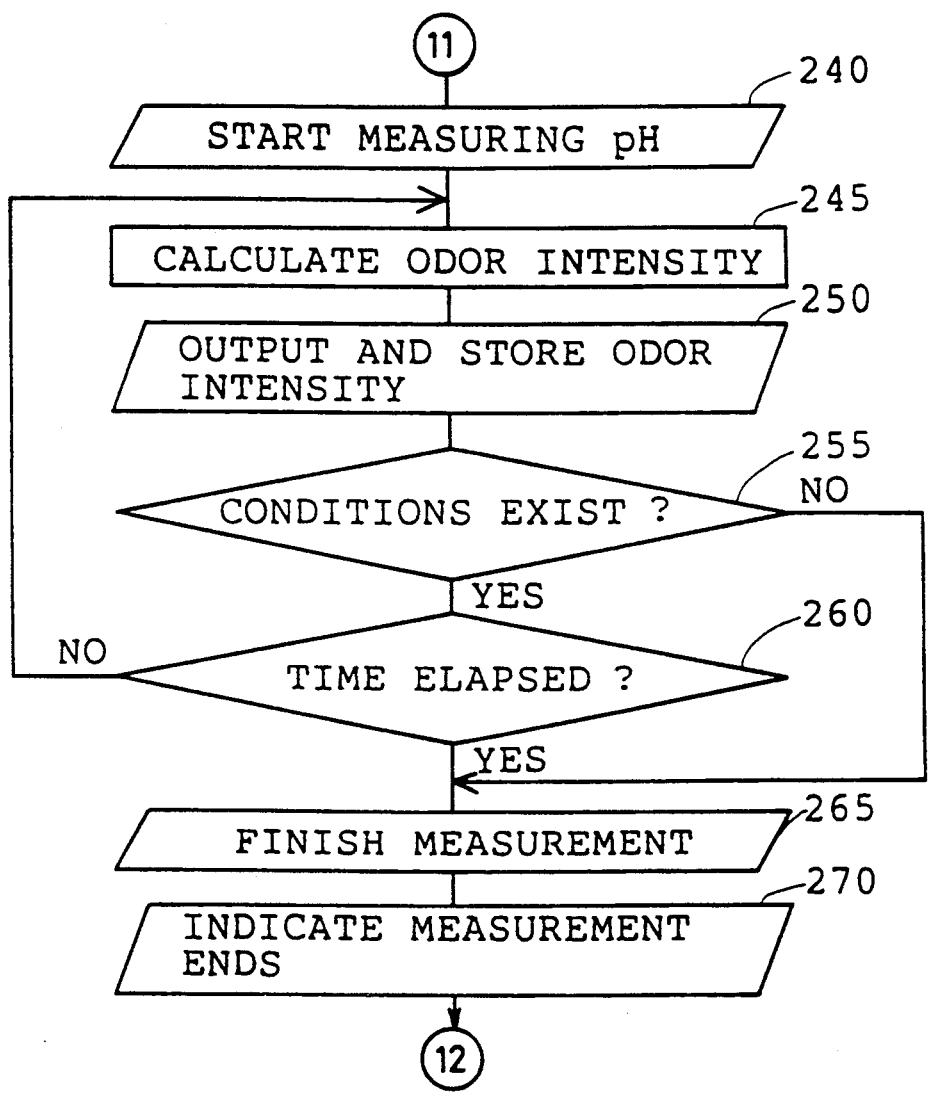

The method for measuring the odor intensity of the exhaust gas is outlined in the flowchart in FIGS. 6A and 6B. When the electronic controller 135 is turned on, the measurement starts.

First, step 200 reads and sets the conditions fed from the input unit 153, such as the desired refrigerant temperature, time period corresponding to the frequency of the continuous measurement, the rate for introducing the exhaust gas, and the rate for supplying demineralized water. Subsequently, step 205 determines whether or not the conditions initialized at step 200 exist. When the conditions exist, the process goes to step 210. When the conditions do not exist, step 205 is repeated until the conditions are set.

At step 210, the electronic controller 135 indicates on the input unit 153 that the exhaust-gas analyzer 131 can start the measurement, and instructs the operator to press a start switch. Subsequently, step 215 determines whether the start switch on the input unit 153 has been pressed and the operation start signal has been issued. Step 215 is repeated until the operation start signal has been issued.

If the operation start signal has been issued, step 220 transmits a control signal to the driving pulley 142a to drive the belt 141, and transmits a control signal to the cooling tank 143 to adjust its temperature to the one read at step 200. Next, step 225 transmits a control signal to the exhaust-gas tank 133, which starts introducing the specimen exhaust gas to the reactor 132 at the rate set at step 200. Step 230 sends a control signal to the water supplier 134 to start supplying demineralized water at the rate set at step 200. Step 235 sends a control signal to the heating drier 150 to start its operation to prepare for another measurement of the pH-value. Through the processes of steps 200 through 235, the belt 141 rotates and passes through the cooling tank 143.

When the cooling tank 143 cools the belt 141, the outer surface of the belt 141 bends so that it is concave. Since the belt 141 has been cooled, only the odor-producing substances on the surface congeal. On the surface of the belt 141, an aqueous solution is prepared from the odor-producing substances in the exhaust gas.

The pH value measuring apparatus 146 then determines the pH value of the aqueous solution on the surface of the belt 141. After the belt 141 passes the pH-value measuring apparatus 146, the belt 141 is cleaned, and is heated to dry and flatten again. Thus, the preparation for another measurement of the pH-value is made.

Subsequently, step 240 sends a control signal to the pH-value measuring apparatus 146, which starts measuring the pH-value. Step 245 calculates the odor intensity Q based on the measured pH-value according to formula (1):

$$Q = pH \cdot K + B \ldots (1)$$

in which K is a compensating constant, and B is a constant. The graph in FIG. 4 pictorially represents the linear relationship between odor intensity Q and pH-value as defined by formula (1).

Subsequently, step 250 transmits a control signal to the printer 154 indicating the odor intensity Q calculated at step 245. The odor intensity Q is also stored in the RAM 135c. Step 255 determines whether the conditions set at step 200 still exist. If the conditions still exist, then the exhaust-gas analyzer 131 is operating normally assuring the continuous measurement of the pH-value, and the process goes to step 260. If the conditions do not exist, the exhaust-gas analyzer 131 has something wrong so it cannot assure the continuous measurement, and the process goes to step 265. Step 260 determines whether or not the time period set at step 200 has elapsed. If the time period has elapsed, the pH-value measurement finishes, and the process goes to step 265. On the other hand, if the answer at step 260 is negative, further measuring is required, and the process returns to step 245.

Step 265 transmits a control signal to the exhaust-gas tank 133, the water supplier 134, the pH-value measuring apparatus 146, the heating drier 150, and the printer 154, directing them to stop their functions. Subsequently, step 270 transmits a control signal to the printer 154 indicating that the measurement has ended, and the process goes back to step 205. In this second embodiment, when the start switch on the input unit 153 is pressed, steps 200–270 are repeated.

The second embodiment has the following attributes in addition to those of the first embodiment. The odor-producing substances in the exhaust gas condense on the surface of the bimetallic belt 141, an aqueous solution is prepared from the substances, the pH-value of the solution is measured, the odor intensity is calculated from the pH-value, and the surface of the belt 141 is cleaned. Since these processes can be continuously implemented, the accuracy of the measurement is enhanced. The second embodiment is most effective when the pH-value is continuously measured while the diesel engine 150 is running.

These are only two possible embodiments of the invention claimed below. These embodiments are only illustrations of the claims, and in no way restrict the scope of the claims.

I claim:

1. An apparatus for assessing odor intensity of combustion gas from an internal combustion engine, comprising:
   a reaction vessel;
   combustion gas delivery means for delivering combustion gas to the reaction vessel;
   water delivery means for delivering water to the reaction vessel;
   means for preparing an aqueous solution from the combustion gas and the water delivered to the pH sensing means for sensing the pH value of the aqueous solution;
   measuring means for initiating and regulating assessment according to a predetermined method, and for assessing an odor intensity based on the pH sensed by the pH sensor according to a predetermined relationship between pH and odor intensity of the combustion gas;
   output means for outputting the odor intensity assessed by the measuring means; and
   waste removal means for removing the aqueous solution from the reaction vessel.

2. The apparatus for assessing the odor intensity of combustion gas from an internal combustion engine as in claim 1, further comprising cooling means for cooling the reaction vessel before the combustion gas delivery means delivers combustion gas to the reaction vessel.

3. The apparatus for assessing the odor intensity of combustion gas from an internal combustion engine as in claim 1, wherein the combustion gas delivery means comprises spraying means for spraying combustion gas on a polar adhesive agent positioned in said reaction vessel.

4. The apparatus for assessing the odor intensity of combustion gas from an internal combustion engine as in claim 1, wherein:
   the water delivery means delivers water to the reaction vessel; and
   the combustion gas delivery means delivers combustion gas to the reaction vessel by releasing bubbles of combustion gas into the water of said reaction vessel, forming an aqueous solution.

5. An apparatus for assessing the odor intensity of combustion gas from an internal combustion engine, comprising:
   a closed belt means;
   belt-driving means;
   shaping means for shaping the belt means so that it forms a trough that opens on an outer surface of the belt means;
   combustion gas delivery means for delivering combustion gas to the trough formed by the belt means;
   water delivery means for delivering water to the trough formed by the belt means to mix with the delivered combustion gas to form a sample;
   waste material removal means for removing the sample from the trough in the belt means;
   pH sensing means for sensing the pH-value of the contents of the trough formed by the belt means;
   belt restoration means;
   electronic control means for initiating and regulating assessment according to a predetermined method, and for assessing an odor intensity based on the pH sensed by the pH sensor according to a predetermined relationship between pH and odor intensity of the combustion gas; and
   output means for outputting the odor intensity assessed by the electronic control means.

6. An apparatus as in claim 5 in which
   the belt means is comprised of a bimetallic material;
   the shaping means comprises cooling means; and
   the belt restoration means comprises means for cleaning, drying, and heating the belt means.

* * * * *

UNITED STATES PATENT AND TRADEMARK OFFICE
CERTIFICATE OF CORRECTION

PATENT NO. : 5,149,504
DATED : September 22, 1992
INVENTOR(S) : Toshiaki TANAKA

It is certified that error appears in the above-identified patent and that said Letters Patent is hereby corrected as shown below:

On the cover page, insert --[73] Assignee: Toyota Jidosha Kabushiki Kaisha, Aichi-ken, Japan--.

Signed and Sealed this

Twenty-first Day of September, 1993

Attest:

BRUCE LEHMAN

Attesting Officer

Commissioner of Patents and Trademarks